United States Patent
Shepard et al.

(10) Patent No.: US 7,554,086 B2
(45) Date of Patent: Jun. 30, 2009

(54) INFRARED CAMERA MEASUREMENT CORRECTION FOR PULSED EXCITATION WITH SUBFRAME DURATION

(75) Inventors: Steven Shepard, Southfield, MI (US); James R. Lhota, Beverly Hills, MI (US)

(73) Assignee: Thermal Wave Imaging, Inc., Ferndale, MI (US)

( * ) Notice: Subject to any disclaimer, the term of this patent is extended or adjusted under 35 U.S.C. 154(b) by 451 days.

(21) Appl. No.: 11/245,917

(22) Filed: Oct. 7, 2005

(65) Prior Publication Data

US 2006/0062561 A1 Mar. 23, 2006

Related U.S. Application Data

(63) Continuation-in-part of application No. 11/189,463, filed on Jul. 26, 2005, now abandoned.

(60) Provisional application No. 60/591,193, filed on Jul. 26, 2004.

(51) Int. Cl.
*G01J 5/02* (2006.01)

(52) U.S. Cl. .................. 250/341.1; 250/341.6; 396/155; 396/392; 374/10

(58) Field of Classification Search .............. 250/341.1, 250/341.6; 396/155, 392
See application file for complete search history.

(56) References Cited

U.S. PATENT DOCUMENTS

| 4,592,639 | A | * | 6/1986 | Nakamura | ................... 396/159 |
|---|---|---|---|---|---|
| 5,497,001 | A | * | 3/1996 | Filo | ........................ 250/316.1 |
| 5,719,395 | A | * | 2/1998 | Lesniak | ...................... 250/330 |
| 6,394,646 | B1 | * | 5/2002 | Ringermacher et al. | ........ 374/7 |
| 6,516,084 | B2 | * | 2/2003 | Shepard | ...................... 382/141 |
| 2002/0172410 | A1 | * | 11/2002 | Shepard | ...................... 382/141 |
| 2003/0193987 | A1 | * | 10/2003 | Zalameda et al. | .............. 374/5 |
| 2005/0056786 | A1 | * | 3/2005 | Shepard et al. | .......... 250/341.4 |

\* cited by examiner

*Primary Examiner*—David P Porta
*Assistant Examiner*—Casey Bryant
(74) *Attorney, Agent, or Firm*—Honigman Miller Schwartz & Cohn LLP

(57) ABSTRACT

A method for measuring the timing of a flash event including capturing a first image prior to the commencement of a flash event. Capturing a second image during the occurrence of the flash event, and comparing the second image to the first image to determine a time related characteristic of the flash event.

24 Claims, 8 Drawing Sheets

Ideal Pulsed Thermography Measurement Timing

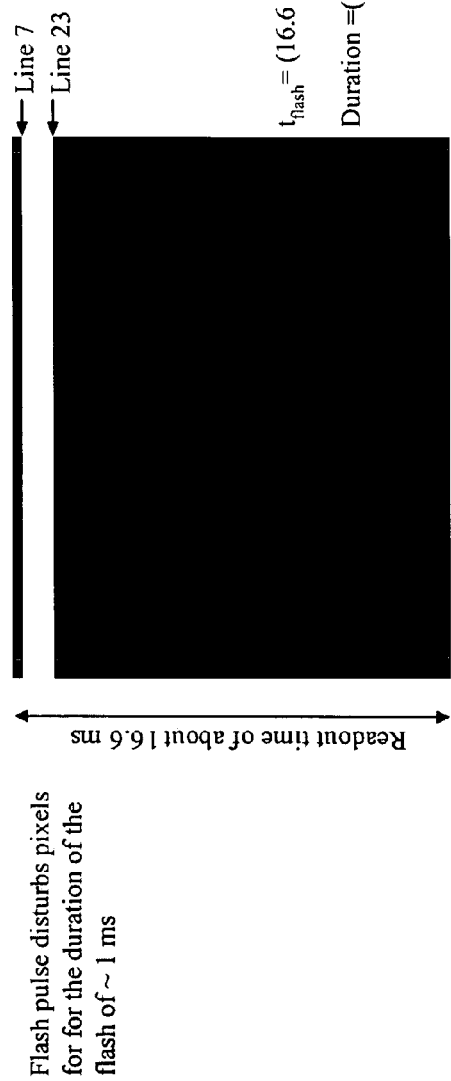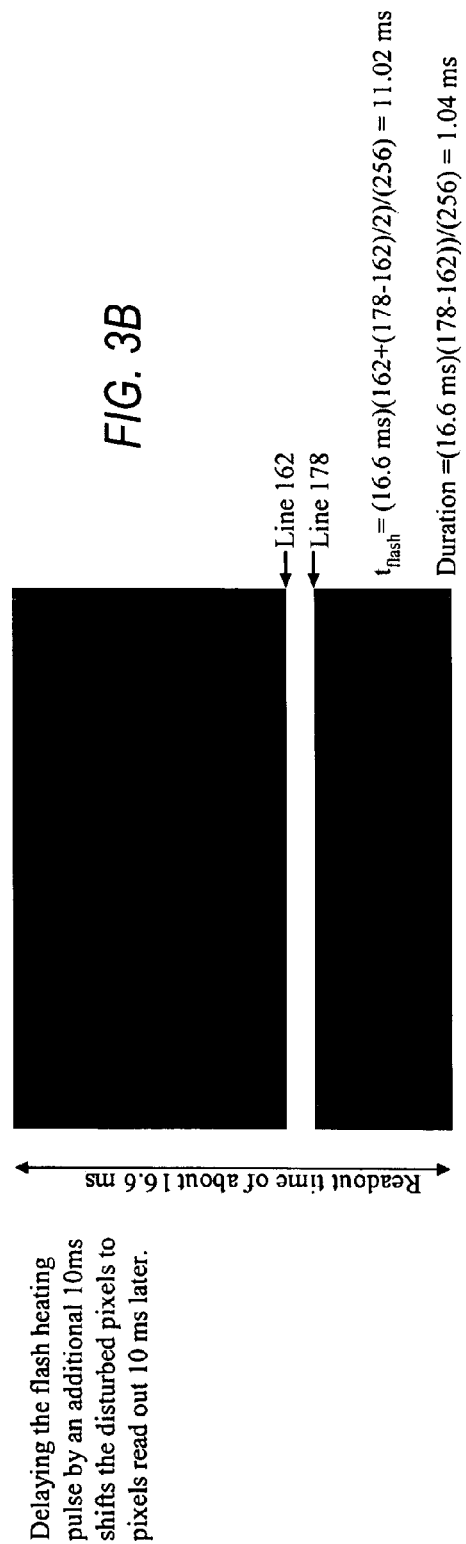

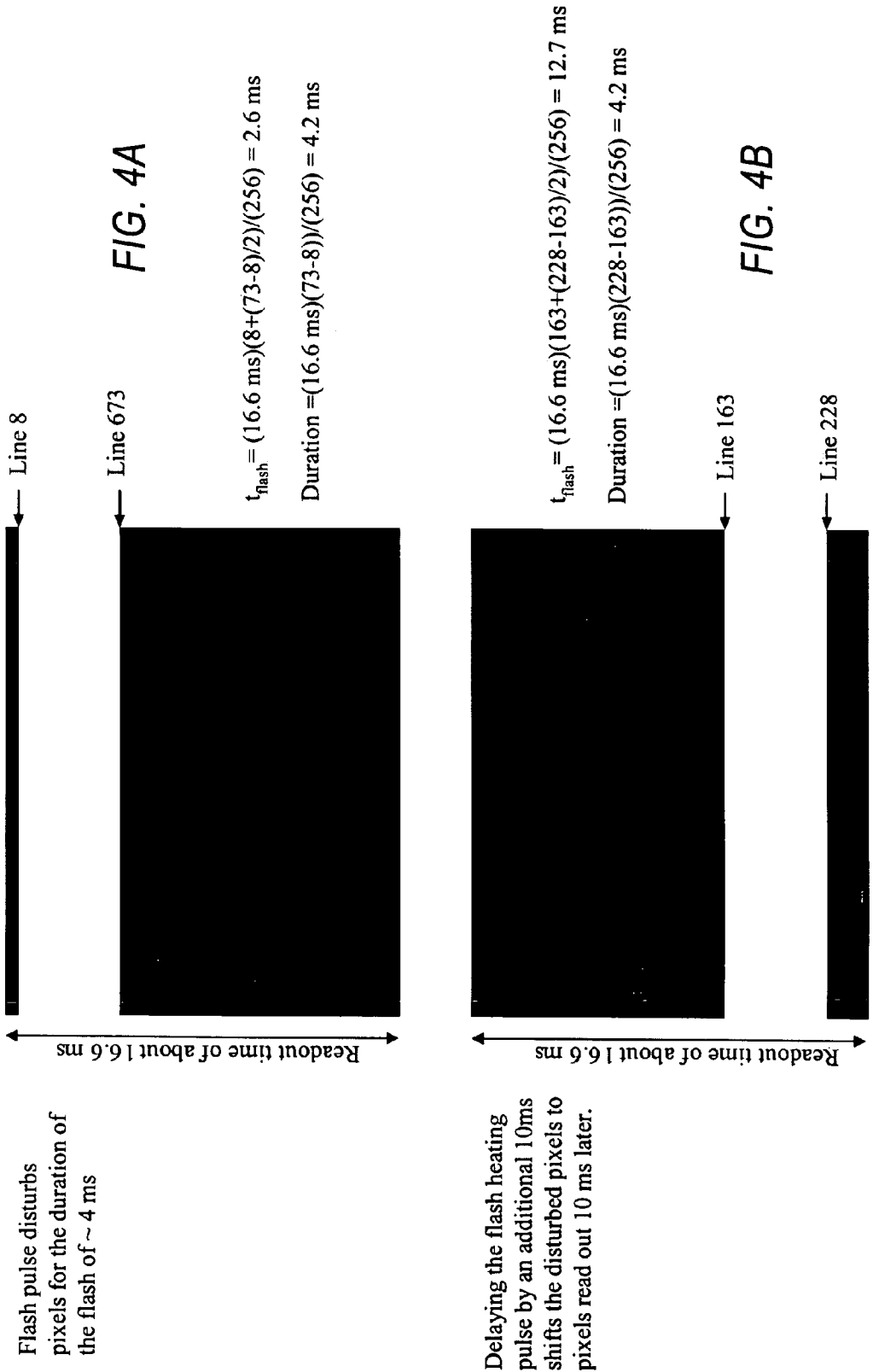

INFRARED CAMERA MEASUREMENT CORRECTION FOR PULSED EXCITATION WITH SUBFRAME DURATION

RELATED APPLICATIONS

This application is a continuation-in-part of U.S. application Ser. No. 11/189,463 filed on Jul. 26, 2005 which claims priority to U.S. provisional application Ser. No. 60/591,193 filed on Jul. 26, 2004.

TECHNICAL FIELD

This invention generally relates to infrared camera measurement systems, and more particularly relates to infrared camera measurement systems used in thermography.

BACKGROUND OF THE INVENTION

Active thermography is used to nondestructively evaluate (NDE) samples in order to detect sub-surface defects. It is effective for uncovering internal bond discontinuities, delaminations, voids, inclusions and other structural defects that are not detectable by visual inspection of the sample. Generally, active thermography involves heating or cooling the sample to create a difference between the temperature of the sample and the ambient temperature and, then observing the infrared thermal signature that emanates from the sample as it returns to a state of thermal equilibrium. Pulsed thermography is widely used in the nondestructive evaluation of component parts used in aerospace and the power generation industry.

An infrared (IR) camera is typically used for thermography to measure the infrared radiation emitted from a sample as it returns toward a steady state temperature. Anomalies in the cooling behavior of the sample are produced when sub-surface defects are present because the sub-surface defects affect the diffusion of heat from the surface of the sample into the body of the sample. In particular, sub-surface defects cause the surface immediately above the defect to cool at a different rate than that of the surrounding (defect-free) areas. As the sample cools, the IR camera captures and records an infrared image of the sample, creating a sequential, time record of the sample's surface temperature.

In performing thermography, it is typically assumed that the integration time, (i.e. the time during which photons are collected by the focal plane array (FPA) detector of the infrared camera), occurs simultaneously with the beginning (i.e. on-set) of the video frame, or, more specifically, with the on-set of frame synchronization pulse (hereinafter frame sync or vertical sync signal). In fact, in many high performance IR cameras typically used in NDT applications, the integration time precedes the frame sync by a percentage of the frame sync period. For example, the integration for a given time frame may occur during the outputting of the previous frame (commonly referred to as "integrate while read mode"). The precise time at which the temperature measurement is made may differ from the apparent time (based on the frame number) by a significant amount. This difference is especially acute in the earliest post-flash frames.

The present invention uses an infrared camera to accurately measure the on-set of the flash event pulse with respect to the frame sync signal. The present invention also uses the infrared camera to measure the duration of the flash pulse event. This is accomplished by detecting a slight disturbance in the pixel values in the frame that is read-out concurrently with the occurrence of the heating pulse.

BRIEF DESCRIPTION OF THE DRAWINGS

FIGS. 3A and 3B is an image formed by subtracting pixel values from Frame 0 from pixel values taken from a prior frame for a 1 ms flash pulse;

FIGS. 4A and 4B is an image formed by subtracting pixel values from Frame 0 from pixel values taken from a prior frame for a 4 ms flash pulse.

DISCLOSURE OF THE INVENTION

Figure 1:
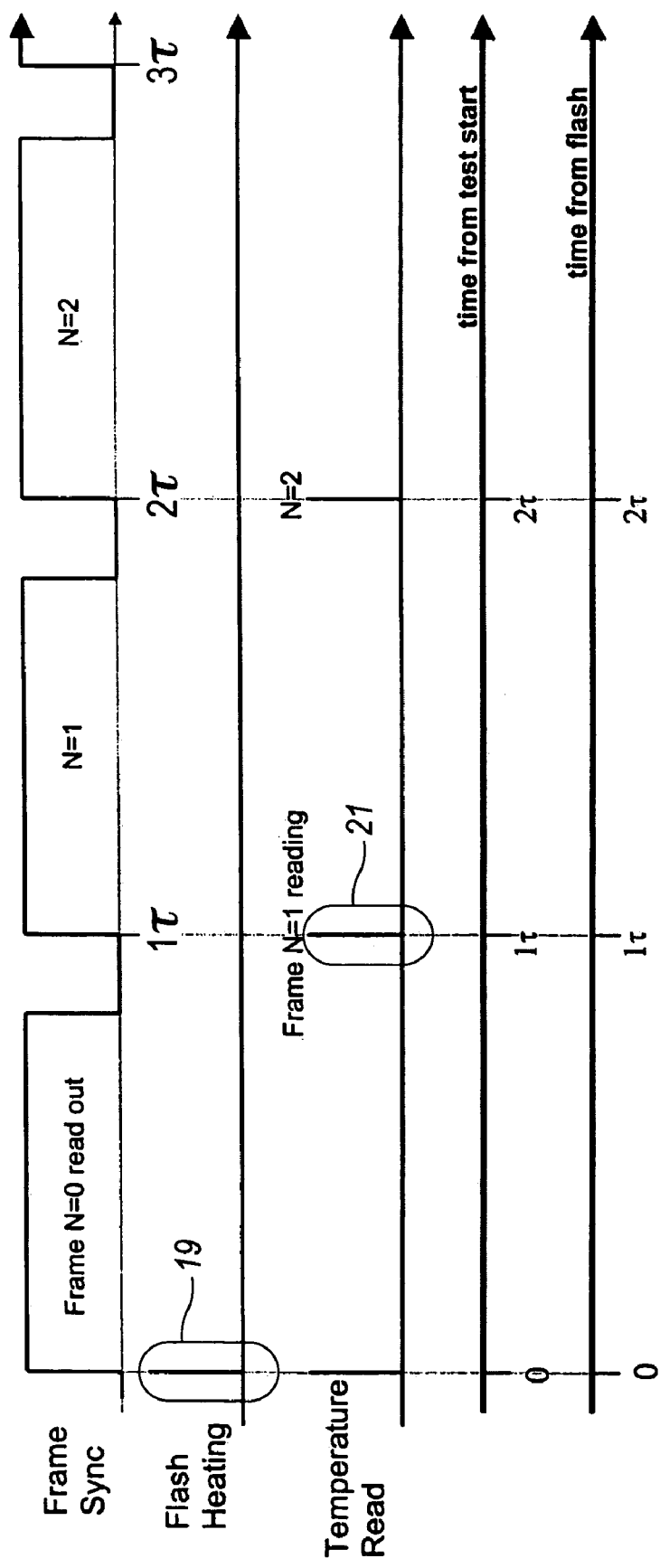
FIG. 1 is an idealized timing diagram of a pulsed thermography measurement.

Now referring to FIG. 1, in most instances, the effect of the timing skew (error) between the flash pulse and the frame sync signal is negligible because, in active thermography NDE applications, temperature does not typically change significantly over an interval defined by two consecutive frames. However, in early post-flash frames of a pulsed thermographic NDT measurement, the error can be considerable. The significance of the error can be illustrated by considering equation (1) below which is the solution to the 1D diffusion equation for surface temperature of a sample following application of an instantaneous, uniform heat pulse:

$$T(t) - T_0 = \frac{Q}{e\sqrt{\pi}\sqrt{t}} \quad (t > 0) \tag{1}$$

wherein T is the temperature of the sample after the application of the heat pulse, $T_0$ is the temperature prior to applying the heat pulse, Q is the heat pulse energy per area of the sample, e is the sample's material property of thermal effusivity, and t is the time after application of the heat pulse.

Using an infrared camera necessitates that the temperature measurements acquired by the camera are acquired at discrete time intervals separated by the frame period τ which is 1/frame rate. Typically, it is assumed that the heating pulse 19 occurs at the rising edge of the Frame Sync signal for frame number N=0 (as depicted in FIG. 1) and that each frames' FPA measurement 21 coincides with the rising edge of its respectively associated Frame Sync signal (the rising edge of each frame N occurs at time t=Nτ after the heating pulse).

In this ideal situation, the surface temperature measurements in the 1D case is:

$$T(N) - T_0 = \frac{Q}{e\sqrt{\pi}\sqrt{N\tau}} \quad (N > 0) \tag{2}$$

This ideal pulse thermography measurement timing discussed above is set forth graphically in FIG. 1.

Figure 2:
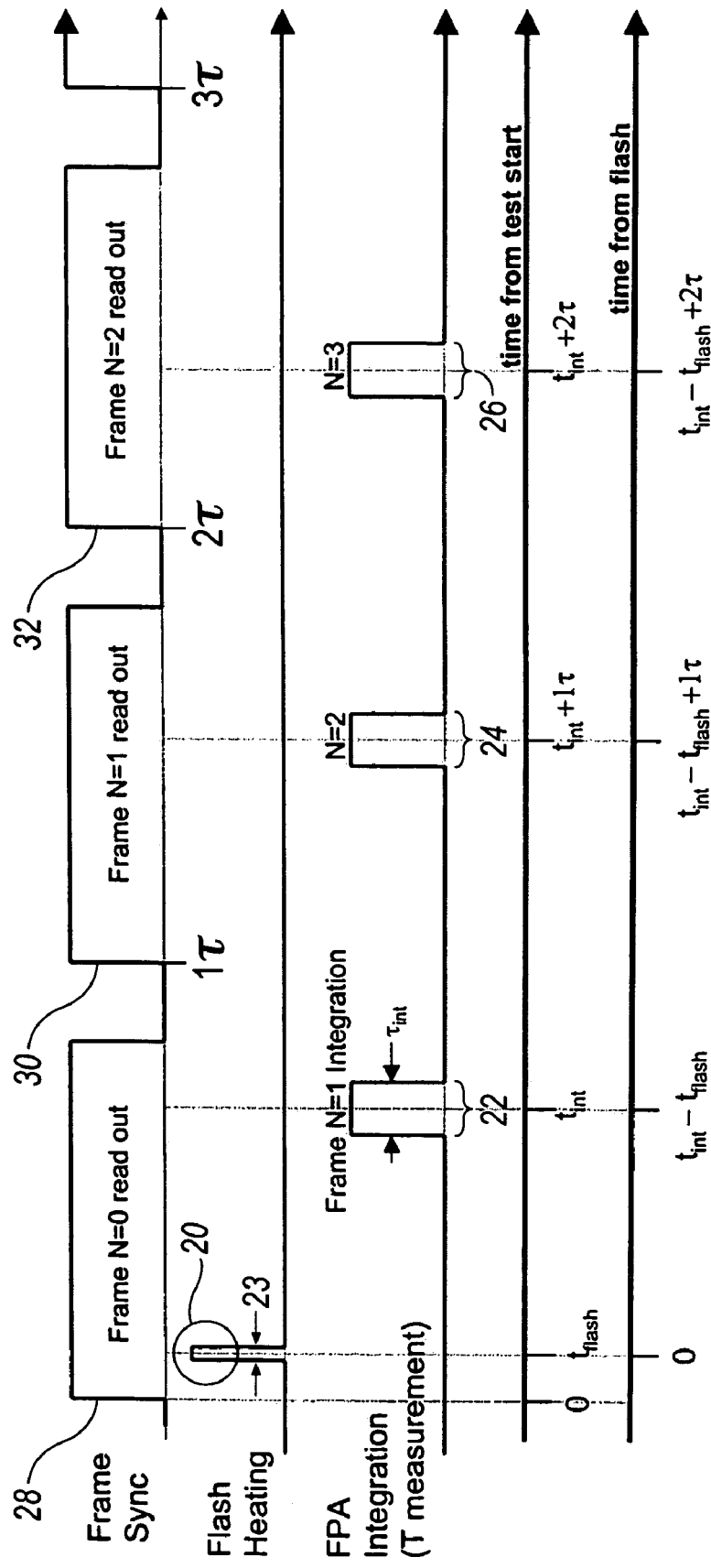
FIG. 2 is a typical, non-idealized, timing diagram of a pulsed thermography measurement.

Although the idealized assumptions referred to above are often sufficient for most NDT measurements, in certain NDT applications, they can lead to significant errors. For example, in most thermographic NDT measurements, the heating pulse 20 (see FIG. 2) and the on-set of the FPA integration periods 22, 24 and 26 are not coincident with the rising edges of the Frame Sync signals 28, 30 and 32. FIG. 2 shows a significant (but typical) time skew between the heating pulse 20, FPA integration periods 22, 24, 26 and the rising edges 28, 30, 32 of the Frame Sync signals. If the flash heating pulse is offset from N=0 Frame Sync by $t_{flash}$ and the integration time for frame N=1 is offset by time $t_{int}$ from N=0, then the correct times from heating pulse to measurement are $t=(N-1)\tau + t_{flash} - t_{int}$. Accordingly, a corrected equation taking into account this offset is as follows:

$$T(N) - T_0 = \frac{Q}{e\sqrt{\pi} \sqrt{(N-1)\tau + t_{int} - t_{flash}}} \quad (3)$$

The differences produced between equation (2) and equation (3) is small for large values of N. However, for early frames (frames close to N=0) the correction set forth in equation (3) has a significant impact in analyzing the thermographic data, such as when analyzing the data using log-log plots, TSR processing, or numeric time derivatives.

In practice, the integration period $\tau_{int}$, 22, 24, 26 for a camera is usually synchronized to the Frame Sync and to the integration offset time tint. However, the precise timing of the on-set of the integration period is considered to be proprietary by many camera manufacturers, and is not always made available to the end-user. However, the timing, $t_{flash}$, of the flash heat pulse 20 is not necessarily synchronized with the Frame Sync. Also, flash offset time, $t_{flash}$ can vary as a function of any number of factors some of which include flash lamp system settings, variations in state of computer hardware and software, and changes in camera settings such as frame rate and frame size.

It is desirable to have a reliable method of measuring the flash pulse offset time, $t_{flash}$, and flash pulse duration 23.

An embodiment of the present invention is effective for detecting the on-set of the heating flash pulse and the flash pulse duration by monitoring the pixel values generated in the frame that is being read-out at the time that the heating pulse is generated. The pixel values read-out during a given frame, are usually comprised of image values that were captured during the integration period of the prior frame (see FIG. 2 wherein N=1 integration period 22, which is output in 30 Frame N=1, takes place during the time that Frame N=0 is read-out).

Infrared cameras are designed to measure only those photons that pass through the camera lens (in the vicinity of the optical axis of the camera lens) during a specified period of time (i.e. the integration period). However, the excitation pulse used in flash thermography is intense (relative to the flux of emitted infrared radiation normally encountered after the flash event), and accordingly, some portion of the flux may leak into the solid-state read-out device either before or after the integration period. This leakage may occur through crevices, translucent surfaces, oblique reflections, or by way of other sources. Regardless of the leakage mechanism, the end result is that the image that is being read-out concurrently with the occurrence of a flash event will comprise both the infrared image of the camera field of view as it existed in the frame immediately prior to the flash event, in combination with a leakage signal contribution to those pixels (of the image) that were being read out while the flash event occurred. The magnitude of the additional leakage signal component is small (approximately 40 parts out of 10,000), and it is a function of the flash amplitude only (i.e. the leakage component is non-imaging—it does not have any correlation to the image that occurs within in the field of view of the infrared camera).

The images acquired immediately before the flash event are identical (except for noise and ambient thermal fluctuations), and show the sample at a steady state temperature. As the last pre-flash frame is being read out, the actual flash event occurs, and the read out frame may be disturbed by leakage flux from the flash. The disturbance is most easily observed by subtracting the pixel values collected from the frame being read-out during the heating pulse with the corresponding pixel value collected from one or more earlier frames. The pixels in a frame are read-out sequentially in time (serially). A pixel's value is only disturbed if a flash occurred simultaneously with that pixel's read-out. For example, if a frame, N=0 is read-out during a heating pulse (see FIG. 2), then subtracting frame N-1 (pixel-by-pixel) from the corresponding pixels in frame N=0, creates an image that highlights the pixels disturbed by the heating pulse (see FIGS. 3A-4B). The flash heating pulse 20 does not disturb any pixels read-out before or after the pulse, thus, the subtracted value is nearly zero. Accordingly, the pixel's value read-out during the flash heating pulse are elevated when they are compared to corresponding pixel values from pre-flash event frames. Subtracting the value of the flash-affected pixels from the value of the corresponding pre-flash affected frames, will result in a value greater than zero.

The result of the subtraction of the pre-flash frame(s) from the flash-affected frames produces, in effect, a non-imaging, real-time trace, of the flash heating pulse intensity since the FPA is read-out row-by-row from top-to-bottom. For example, if a FPA camera has 200 rows and each row is read-out in 20 ms, and the higher pixel values are observed in rows 40-50, then the $t_{flash}=(20\text{ ms})(40+(50-40)/2)/(200)=4.5$ ms and the detectable flash duration is $(20\text{ ms})(50-40)/200=1$ ms. Although subtraction (as mentioned above) is an effective method of comparing pre-flash pixel values with pixel values collected during the flash event, other method of mathematical manipulation (i.e. division, and the like) are also suitable alternatives.

A graphic manifestation of the implementation of the method of the present invention is set forth in FIGS. 3A, 3B, 4A and 4B. Specifically, the depiction of FIG. 3A shows a graphic image constructed from data captured by a infrared camera using an approximately 1 ms wide flash pulse. Using the techniques set forth above, it can be determined from this graphic representation that the mid-point of the flash occurred 0.97 ms after the commencement of the frame (i.e. $t_{flash}=0.97$ ms) and the duration 23 of the pulse event equals 1.04 ms. In contrast to FIG. 3A, FIG. 3B depicts a flash pulse event of approximately 1.04 ms in duration (same as FIG. 3A); however, the on-set of $t_{flash}$ occurs at 11.02 ms representing an on-set delay of the flash pulse by approximately 10 ms later than that shown in FIG. 3A. By comparing FIG. 3B with 3A, $t_{flash}$ can easily be determined using the methods disclosed herein without using anything other than information made available by the infrared camera. The graphic representation for extremely short durations will not manifest themselves as horizontal bands (as shown in FIGS. 3A-4B) but rather as one or more, adjacent illuminated pixels.

FIGS. 4A and 4B show a similar delay to that of FIGS. 3A and 3B (i.e. FIG. 4A shows a mid-point delay of approximately 2.6 ms and FIG. 4B shows a delay of approximately 12.7 ms), however, the flash duration in FIGS. 4A and 4B has been changed to 4.2 ms (as compared to the flash duration in FIGS. 3A and 3B which is approximately 1 ms). This increase in pulse duration from 1.04 ms to 4.2 ms manifests itself visually as a much wider strip.

In thermographic non-destructive testing, infrared radiation that is emitted from the sample surface is used to infer the presence or properties of sub-surface features within the sample. However, for frames acquired during the actual occurrence of the flash-pulse, the infrared camera detector may be saturated by the intense infrared component that is either the result of reflected pulse energy (reflected from either the sample surface or the background surrounding the sample), or stray energy from the flash-pulse that is collected by the camera. Because saturated frames contain no useful information about the field of view and interfere with normal inspection procedures, they are normally considered undesirable. Even if complete saturation does not occur, the direct collection of photons from a flash-pulse may artificially increase the amplitude of all pixels in the first frame of the heated image thereby causing misleading results. In practice, the most common solution to the saturation problem (and often, the only available solution) is to reduce the flash energy to a level that will not cause direct saturation of the infrared camera being used. Reducing flash energy can be accomplished by either reducing the amount of electrical energy stored in the flash power supply discharge capacitor, or by shortening the flash-pulse duration. Shortening the flash-pulse duration can be done either electronically or mechanically (i.e. with a mechanical shutter). However, even though the above-referenced techniques can be used to considerably lower the incident flux, saturation may still occur in the earliest frame. This occurs when all or part of the flash pulse takes place simultaneously with all or part of the detector integration period. In fact, in many cases, it is possible to avoid saturation altogether without reducing flash energy by simply timing the flash-pulse event so that part of the flash-pulse event does not coincide with any portion of the integration period. A device for offsetting the on-set of a pulse event is set forth in U.S. patent application Ser. No. 10/902,225 which is hereby incorporated by reference.

Typically, the timing of the on-set and duration of the flash event with respect to the timing of the frame is not precisely defined or controlled and it is often assumed that the on-set of the flash event coincides with the on-set of frame 0 at t=0. Therefore, the timing of subsequent frames is referenced by the product of the frame period and the frame number under consideration. Normal convention assumes that the flash event occurs during frame 0. For example, a camera with a 60 Hz frame rate (i.e. 16.66 msec per frame) would be described as capturing the flash event at 0 seconds, a first frame at 16.66 msec, a second frame at 3.332 msec, etc. In fact, these numbers do not precisely describe the situation inasmuch as a flash occurring at t=0 implies that the flash event coincided precisely with the on-set of the integration period. Such precise timing is unlikely to occur unless mechanisms are in place force the synchronization of the flash event and the integration period. Furthermore, as discussed above, it is highly likely that a frame which is acquired during the concurrent application of a flash event will be saturated.

The physical phenomena discussed herein are influenced by the flash event which may be timed to occur at t=0. The infrared camera is primarily used to record infrared stimulus and so the fact that the infrared camera can be used to infer flash timing is merely an artifact. However, this artifact can be used to glean information about, and to manipulate, the timing relationship between the integration period, the flash event, and the frame.

Figure 5:
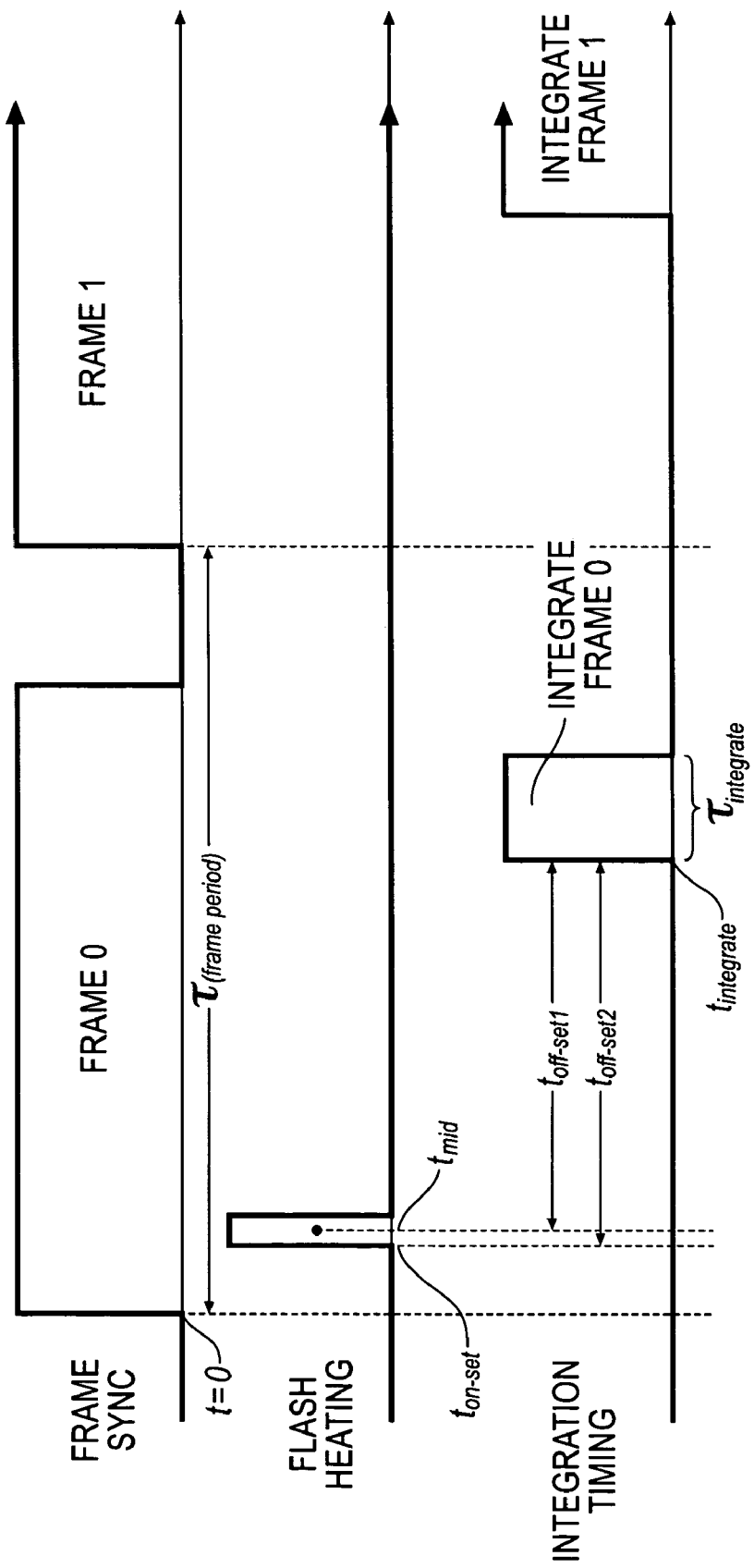
FIG. 5 is a timing diagram showing the relative timing between a frame synchronization pulse, a flash heating pulse, and an integration timing pulse.

Now referring to FIG. 5, if the on-set of the actual flash pulse (see $t_{on\text{-}set}$ FIG. 5) occurs 3 msec before the commencement of the associated integration period (see $t_{integrate}$), it is more accurate to state that the on-set of the associated frame (Frame 0 in FIG. 5) occurred at t=3 msec (not t=0). Subsequent Frames would commence at time 19.66 msec, 36.33 msec, etc., according to the formula:

$$t_{frame\ N} = [\text{Frame number} * \text{frame period}] + \text{flash offset} \quad (4)$$

wherein, $t_{frame\ N}$ is the on-set of the nth Frame;

Frame number is the number of the Nth Frame (by definition, the first Frame is Frame N=0); and frame period is equal to the time it takes to complete one frame cycle (all Frames are assumed to have periods of identical duration).

Flash offset is equal to the time difference between the on-set of the integration period ($t_{integrate}$) and the on-set of the flash heating event, or, in an alternative embodiment, flash offset is equal to the difference between the on-set of the integration period ($t_{integrate}$) and the median time ($t_{mid}$) of the flash heating event.

The flash heating event marks the beginning of the physical phenomena of interest and accordingly the on-set of the flash or alternatively the median point of the flash could be designated t=0. The collection of photons by the infrared camera is an external event that does not effect the physical process of interest. For accurate characterization of the signals selected from the infrared camera, the timing of the integration (i.e. the time value assigned to each frame) should be measured with respect to the on-set of the flash event irrespective of the on-set of the frame. Using the correct timing or the integration frames is extremely advantageous for measurement or analysis of near surface features.

It is possible to exploit the fact that precise timing between the pulse event and the integration time can be measured and controlled (using a flash truncation and synchronization device). In particular, it is possible to create a quasi-high-frame-rate image using a relatively low-frame-rate camera. This can be accomplished by acquiring at least two different sequences wherein, for each sequence, the flash heating pulse event precedes the on-set of the integration period by a different duration (i.e. for the first sequence, the pulse event precedes the on-set of the integration period by N×Tsec; for the second sequence the on-set of the pulse event precedes the on-set of the integration period by 2×Tsec, etc.). Thereafter, the images captured during the integration periods associated with each sequence are sequentially ordered (interleaved based on time). Thus, even though a camera with a 60 Hz frame rate is only capable of acquiring a frame every 16.66 msec, acquiring sequences with offsets of 0 msec and 8.33 msec, respectively, would, when joined, create a composite sequence with an effective frame rate of 120 Hz. Higher effective frame rates could be achieved with additional sequences and offsets. Various thermographic reconstruction techniques could then be applied to build a continuous data sequence from the constituent sequences. Techniques for building a continuous data sequence are set forth in U.S. patent application Ser. No. 10/848,274 filed May 18, 2004, U.S. Pat. Nos. 6,751,342 and 6,516,084.

Disclosed herein is a system for measuring the duration and on-set of a flash event relative to the timing of a video frame by exploiting the leakage of the flash event into the frame that is read-out concurrently with occurrence of the flash event. Also disclosed herein is a technique for eliminating saturation of early frames by intentionally off-setting the flash duration from the integration period. The duration of the integration period is usually provided to the user by the camera manufacturer, and in some camera models, it can be programmed by the user. However, the precise timing of the on-set of the integration period (within the video frame) is often considered to be proprietary by camera manufacturers and it may not be made available to camera users. In such cases, it is necessary to determine experimentally, the on-set of the integration period. The techniques disclosed herein can be used to measure the on-set of the integration event and the duration of the integration event period by further exploiting the leakage phenomena discussed herein. The on-set of the integration event and the duration of the integration event are referred to collectively herein as integration timing. One embodiment of a method for measuring the integration timing is set forth in FIGS. 6, 7A, and 7B.

Figure 6:
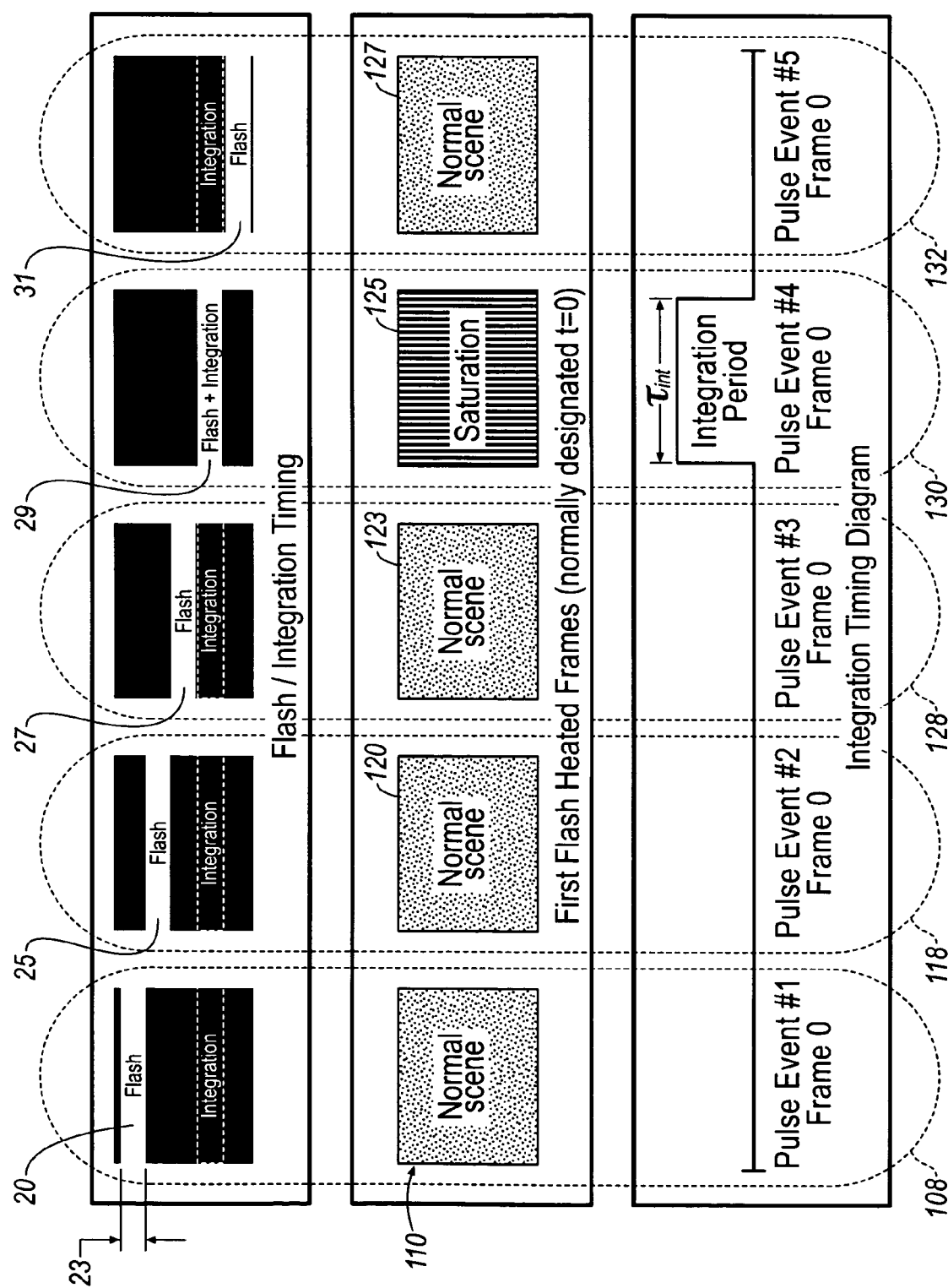
FIG. 6 sets forth a graphical depiction of a scheme to measure camera integration time.
Figure 7A:
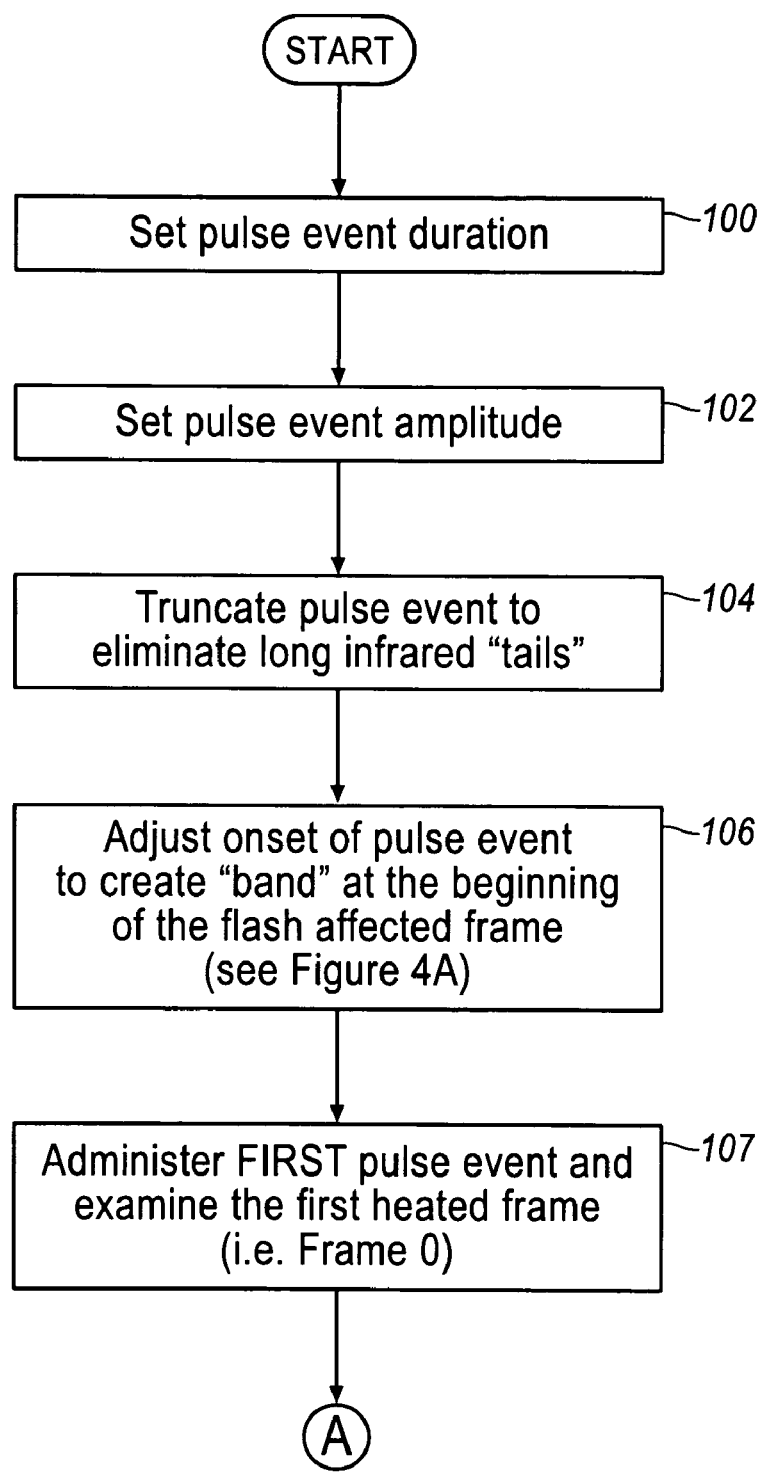
FIGS. 7A and 7B are a flow diagram setting forth method steps for measuring camera integration time.
Figure 7B:
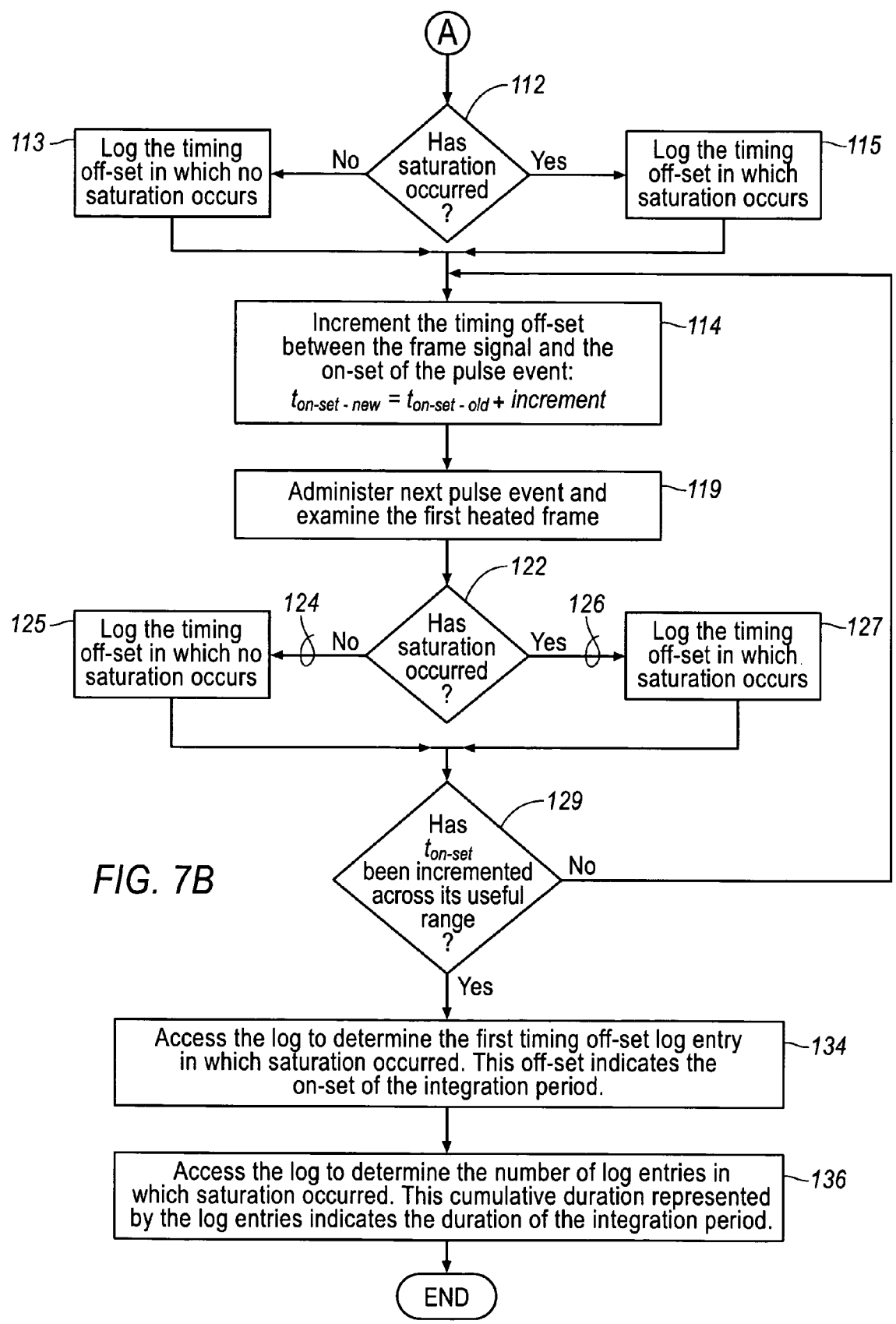

Now referring to FIG. 6, FIG. 7A, and 7B firstly, in step 100 the pulse duration of the flash pulse event should be established to a value less than or equal to the integration period $\tau_{int}$ of the infrared camera (flash duration shown graphically at reference numeral 23 in FIG. 6). Next, the amplitude of the pulse event should be set sufficiently low such that saturation is eliminated from the earliest heated frame (this assumes that the pulse event and the integration period do not coincide—typically a number of "test shots" are required in order to eliminate overlap between the pulse event and the integration period of the camera). Next 104 the pulse event should be truncated so that a long infrared "tail" does not occur. Next 106 the on-set of the pulse 20 should be set so that the flash creates a timing band (see FIG. 3*a*) at or toward the top (i.e. the beginning) of the flash affected frame. Next, 107, 108 a first pulse event is administered and the first flash-heated frame is examined 110 (see FIGS. 6 and 7A). If no saturation (or anomalous amplitude increase effecting all pixels) occurs 112 (FIG. 7B) in the first heated frame 110, the timing offset between the flash pulse event and the integration period does not overlap. The timing offset value along with the fact that no saturation occurred, is logged 113. If there is evidence of saturation (or anomalous amplitude increase), the timing offset value along with the fact that saturation occurred, is logged 115. Next, 114 the timing offset (between the on-set of the frame sync and the on-set of the pulse event) is incremented (i.e. $t_{on\text{-}set\text{-}new} = t_{on\text{-}set\text{-}old} +$increment value) while the duration of the pulse event is left unchanged.

Preferably the increase in the timing offset is adjusted in increments that are less than or equal to the flash duration 23. The next pulse event 118, 119 is initiated at the time dictated by the most recently calculated $t_{on\text{-}set\text{-}new}$ value. The scene 120 is evaluated for saturation 122. If no saturation occurs 124, the appropriate log event is made 125. If saturation does occur 126, the appropriate log event is made 127. If $t_{on\text{-}set}$ has not yet been incremented across its useful range 129, $t_{on\text{-}set\text{-}new}$ is incremented once again (step 114) and a new pulse event is administered 119 using the updated $t_{on\text{-}set\text{-}new}$ values to control the timing of the respectively associated flashes 20, 25, 27, 29, 31. If $t_{on\text{-}set}$ has been incremented across its useful range 129, the log entries created in 113, 115, 125, 127 are examined to determine the earliest timing off-set for which saturation occurred 134. This earliest timing off-set value for which saturation occurred represents the on-set of the integration period. Next, log entries 113, 115, 125, 127 are examined to determine the number and timing of all log entries in which saturation occurred 136. The collective time span represented by the log entries in which saturation occurred represent the duration of the integration period.

The scenes generated 110, 120, 123, 125, 127 for each respectively associated pulse events 108, 118, 128, 130, 132, can be used to determine if saturation occurs during any one of the scenes (saturation occurs in scene 125 FIG. 6).

Optionally, a timing diagram can be constructed using the log entries 113, 115, 125, 127 to construct the on-set and duration of the integration period relative to the start of the frame. It is also noted that a more precise timing determination can be made by creating a reduced flash duration and also by reducing the size of the increments in which the flash timing offset is increased in step 114.

While various embodiments of the invention have been described herein in connection with the invention, it is to be understood that the embodiments disclosed herein are so disclosed by way of illustration and not by way of limitation. The scope of the appended claims should be construed as broadly as the prior art will permit.

What is claimed as new and desired to be protected by Letters Patent of the United States is:

1. A method for measuring the timing of a flash period, comprising the steps of:
   using an infrared camera to capture a first image prior to the commencement of the flash period,
   using said infrared camera to capture a second image during the occurrence of the flash period,
   comparing the second image to the first image to determine a time related characteristic of the flash period, wherein said infrared camera includes a first and second mode of image capturing, wherein said first mode of image capturing includes an integration period and wherein said second mode of image capturing includes a non-integration period, wherein at least one of said first and second image is at least partially captured during the non-integration period of operation of said infrared camera.

2. The method for measuring the timing of a flash period of claim 1, wherein the first image includes a plurality of first image pixel values and said second image includes a plurality of second image pixel values.

3. The method for measuring the timing of a flash period of claim 2, wherein said comparing step includes subtracting at least some of said first image pixel values from at least some of said second image pixel values.

4. The method for measuring the timing of a flash period of claim 2, wherein said comparing step includes subtracting at least some of said second image pixel values from at least some of said first image pixel values.

5. The method for measuring the timing of a flash period of claim 1, wherein said first image is formed from a plurality of images captured prior to the commencement of the flash period.

6. The method for measuring the timing of a flash period of claim 5, wherein said plurality of images are averaged together to form said first image.

7. The method for measuring the timing of a flash period of claim 1, wherein the time related characteristic is a time difference between the on-set of the flash period and a frame sync signal.

8. The method for measuring the timing of a flash period of claim 1, wherein the time related characteristic is a time duration of the flash period.

9. A method for measuring the timing of a flash event using an infrared camera, comprising the steps of:
   using the infrared camera to capture a first sample image prior to the commencement of the flash event,
   using the infrared camera to capture a second sample image during the occurrence of the flash event,
   comparing the second sample image to the first sample image to determine a time related characteristic of the flash event, wherein said infrared camera includes a first and second mode of image capturing, wherein said first mode of image capturing includes an integration period and wherein said second mode of image capturing includes a non-integration period, wherein at least one of said first and second image is at least partially captured during the non-integration period of operation of said infrared camera.

10. The method for measuring the timing of a flash event of claim 9, wherein the first sample image includes a plurality of first image pixel values and said second sample image includes a plurality of second image pixel values.

11. The method for measuring the timing of a flash event of claim 10, wherein said comparing step includes mathematically manipulating at least some of said first image pixel values with respect to at least some of said second image pixel values.

12. The method for measuring the timing of a flash event of claim 11, wherein said mathematical manipulation includes at least one of subtraction or division.

13. The method for measuring the timing of a flash event of claim 9, wherein said comparing step includes subtracting at least some of said second image pixel values from at least some of said first image pixel values.

14. The method for measuring the timing of a flash event of claim 9, wherein said first image is formed from a plurality of images captured prior to the commencement of the flash event.

15. The method for measuring the timing of a flash event of claim 14, wherein said plurality of images are averaged together to form said first image.

16. The method for measuring the timing of a flash event of claim 9, wherein the time related characteristic is a time difference between the on-set of the flash event and a frame sync signal.

17. The method for measuring the timing of a flash event of claim 9, wherein the time related characteristic is a time duration of the flash event.

18. Method for determining integration timing of an integration event carried out by an infrared camera, comprising the steps of:
    establishing at least one time based characteristic of a flash event,
    administering at least one flash event,
    using said camera to capture an attribute of said flash event,
    associating a saturation condition and a timing characteristic with said captured attribute,
    using said saturation condition and said timing characteristic of said captured attribute to determine integration timing.

19. The method of claim 18, wherein integration timing includes at least one of an on-set of said integration event or a duration of said integration event.

20. Method of measuring a time based characteristic of an integration event associated with an infrared camera, comprising the steps of:
    A) setting a duration of a pulse event less than or equal to a duration of said integration event,
    B) initiating at least one pulse event,
    C) capturing an attribute of said at least one pulse event using said infrared camera,
    D) examining at least a first frame associated with an output data produced by said infrared camera,
    E) using said output data to determine at least one of an on-set or duration of said integration event,
    F) wherein at least a portion of the at least one pulse event occurs, simultaneously, with at least a portion of said integration event.

21. The method of claim 20, wherein said step B) further includes initiating a plurality of pulse events.

22. The method of claim 21, wherein each pulse event in said plurality of pulse events has a time value measured relative to a time characteristic of a respectively associated frame signal, wherein the difference between each pulse event's time value and the time characteristic of each respective frame signal defines a delay time value respectively associated with each pulse event in said plurality of pulse events.

23. The method of claim 22, wherein at least some of said delay time values differ from one another by uniform increments.

24. The method of claim 22, further including the step of:
    using at least one of said delay times to determine an on-set of an integration event associated with integration timing, and
    using a combination of two or more delay times to determine a duration an integration event associated with said integration timing.

\* \* \* \* \*